(12) United States Patent
Kitagawa (10) Patent No.: US 6,513,716 B2
(45) Date of Patent: Feb. 4, 2003

(54) AUTOMATIC APPARATUS FOR READING BAR CODES AND AN AUTOMATIC ANALYZER PROVIDED THEREWITH

(75) Inventor: Nobuhiro Kitagawa, Akashi (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 09/839,243

(22) Filed: Apr. 23, 2001

(65) Prior Publication Data

US 2001/0048029 A1 Dec. 6, 2001

(30) Foreign Application Priority Data

May 29, 2000 (JP) ........................................ 2000-158316

(51) Int. Cl.⁷ ................................................ G06K 7/10
(52) U.S. Cl. .................................. 235/462.43; 235/375
(58) Field of Search .......... 235/462.25, 462.01–462.24, 235/462.26–462.45, 472, 375, 494

(56) References Cited

U.S. PATENT DOCUMENTS

| | | | | |
|---|---|---|---|---|
| 5,043,854 A | * | 8/1991 | Gammache | 362/197 |
| 5,471,042 A | * | 11/1995 | Kirkeby et al. | 235/472 |
| 5,477,044 A | * | 12/1995 | Aragon | 235/472 |
| 5,479,002 A | * | 12/1995 | Heiman et al. | 235/472 |
| 5,726,434 A | * | 3/1998 | Seo | 235/472 |
| 5,750,975 A | * | 5/1998 | Myerson et al. | 235/472 |
| 6,164,546 A | * | 12/2000 | Kumagai et al. | 235/472.01 |
| 6,209,789 B1 | * | 4/2001 | Amundsen et al. | 235/472.01 |

FOREIGN PATENT DOCUMENTS

JP          A589277          4/1993

* cited by examiner

*Primary Examiner*—Thien M. Le
(74) *Attorney, Agent, or Firm*—Birch, Stewart, Kolasch & Birch, LLP (57) ABSTRACT

An automatic apparatus for reading bar codes consists of a bar code reader, a reflecting member for reflecting light irradiated from the bar code reader to a bar code, a driving member for moving the reflecting member on a travel path parallel to the direction of the irradiated light and at least one abutment part provided on the travel path. A first container setting part for setting first containers and a second container setting part for setting second containers are arranged on both sides, respectively, of the travel path, and the reflecting member may rotate between a first position to allow the bar code reader to reader first bar codes of the first containers through the reflecting member and a second position to allow the bar code reader to read second bar codes of the second containers through the reflecting member.

19 Claims, 6 Drawing Sheets

AUTOMATIC APPARATUS FOR READING BAR CODES AND AN AUTOMATIC ANALYZER PROVIDED THEREWITH

BACKGROUND OF THE INVENTION

1. Field of the Invention

The present invention relates to an apparatus for reading bar codes stuck to containers set at a plurality of setting parts, and more particularly to an apparatus for reading bar codes stuck to reagent containers/specimen containers and the automatic analyzer provided therewith.

2. Prior Art

In analysis of biological samples (specimens) such as blood, depending on an analytical purpose, a required reagent is taken out from various reagents and added to a specimen, and an optical analysis, for instance, an absorbancy analysis is performed. In recent years, in many of such biological sample analyses, a great number of reagent containers are lined on a reagent rack and the like, and a required reagent is taken out from the reagent containers, and many kinds of analyses are performed. In such a case, it is often observed that a required reagent is identified by previously sticking bar codes to reagent containers and moving the reagent containers or a bar code reader in succession to a position to allow reading the bar codes to read the bar codes with a bar code reader.

And, in an automatic analyzer, it is often observed that to speed the treatment of specimens, a great number of specimen containers are lined on a specimen rack, and bar codes are previously stuck to specimen containers, and the specimen containers or a bar code reader are moved in succession to a position to allow reading the bar codes to read the bar codes with a bar code reader.

In reading bar codes stuck to reagent containers and bar codes stuck to specimen containers, there were required one set of a bar code reader for identification of reagents and a driving means thereof and one set of a bar code reader for identification of specimens and a driving means thereof, i.e., two set of equipments in total. Further, when both bar codes are read with one bar code reader, it is necessary to set a specimen container and a reagent container at the same container setting part and therefore a position where container was set was limited. Therefore, the apparatus became complex and large and the cost was increased.

To solve this problem, the invention of Japanese Patent Application No. Hei 3-276667 (Japanese Unexamined Patent Publication No. Hei 5-89277) was proposed. This invention relates to a biochemical automatic analyzer consisting of a reflector which is arranged between one reagent box where many reagents are arranged and the other reagent box adjacent to the one reagent box and reflects bar codes stuck to reagents in these reagent boxes at a certain angle, a driving device which rotates and drives the reflector, and a bar code reader which senses the position of incidence of the reflected light of the bar code from said reflector and is operated simultaneously with incidence of this reflected light.

In accordance with this invention, although it is possible to read bar codes stuck to containers held at different container holding parts with one bar code reader, it is required to move the containers to the specified position because a position of a bar code reader is fixed, and further it is required to locate two rows of containers at opposite positions relative to a reflecting member, and therefore the position of a container holding part is still limited. Further, since there were required one driving means for moving the reagent containers in succession to a position to allow reading the bar codes per each container holding part and one driving means for rotating a reflecting member and therefore three driving means in total, the foregoing problems of the prior art were still to be resolved and the apparatus became complex and large and the cost was increased.

SUMMARY OF THE INVENTION

Considering these problems, the present invention has been intended, and it is an object of the present invention to provide an automatic apparatus for reading bar codes, which may identify the bar codes stuck to two kinds of containers with a simple constitution and has a high degree of flexibility in an arrangement of containers, and to realize the simplification, the miniaturization and the lower prices of the apparatus. Further, it is an another object to provide an automatic analyzer provided with such an automatic apparatus for reading bar codes.

In accordance with the present invention, there is provided an automatic apparatus for reading bar codes comprising a bar code reader for reading bar codes stuck to containers, a reflecting member for reflecting light irradiated from the bar code reader to the bar codes, a driving means for moving the reflecting member to and from in the direction of the light irradiated from the bar code reader and in the reverse direction thereof on a travel path parallel to the direction of the irradiated light and at least one abutment part provided on said travel path for regulating the range of travel of the reflecting member, wherein a first container setting part for setting first containers stuck with first bar codes and a second container setting part for setting second containers stuck with second bar codes are arranged on both sides, respectively, of said travel path; the reflecting member is provided in such a way that the reflecting member may rotate between a first position to allow said bar code reader to read the first bar codes of the first containers set at the first container setting part through the medium of the reflecting member and a second position to allow said bar code reader to read the second bar codes of the second containers set at the second container setting part through the medium of the reflecting member; and by moving the reflecting member to and from in said way with said driving means, the reflecting member contacts said abutment part to rotate from said first position to said second position or from said second position to said first position and thereby said bar code reader reads the first bar codes and the second bar codes.

According to such an apparatus, it becomes possible to read both bar codes stuck to first containers and second containers with one bar code reader and one driving means, and it becomes unnecessary to locate the first containers and the second containers at opposite positions relative to the reflecting member and therefore a degree of flexibility in an arrangement of containers is enhanced.

BRIEF DESCRIPTION OF THE DRAWINGS

FIG. 9 is a top plan view of a bar code reader and a reflecting member used in the automatic apparatus for reading bar codes of the embodiment of the present invention and FIGS. 9(a), 9(b) and 9(c) are shown in order of sequential motion.

DETAILED DESCRIPTION OF THE PREFERRED EMBODIMENT

In this invention, as a reflecting member, for instance, a reflecting mirror is preferably used. This reflecting mirror is provided rotatably around, for instance, the vertical axis of rotation.

As a driving means, for instance, a stepping motor for driving a power transmission belt is preferably used. The reason why a stepping motor is used is that it becomes easy to stop a desired member (for instance, the reflecting member) at a desired position.

As first containers, for instance, specimen containers for containing specimen are used and, as second containers, for instance, reagent containers for containing reagent are used and, as a first container setting part, for instance, a specimen rack for setting a plurality of specimen containers is used and, as a second container setting part, for instance, a reagent rack for setting a plurality of reagent containers is used.

In this invention, though it is not required to move said bar code reader, it is preferable to move said reflecting member and said bar code reader simultaneously with said driving means from the viewpoint of increasing the reading accuracy by keeping the distance between said bar code reader and said reflecting member, i.e., between a bar code and said bar code reader constant. Accordingly, it is preferred that said reflecting member and said bar code reader are integrated into one.

Preferably, an abutment part consists of a first abutment part at which the reflecting member takes said first position and a second abutment part at which the reflecting member takes said second position to limit the both ends of the range of travel of the reflecting member.

Further, it is preferred that an automatic apparatus for reading bar codes of the invention further comprises a fixation member for fixing said reflecting member at said first position and said second position. Thereby, it becomes free of a self-rotation of said reflecting member due to vibrations from travel of said reflecting member and reliability of the apparatus may be ensured.

Preferably, this fixation member is a mounting hardware integrated with the reflecting member, including a first flat face part being pressed by a plate spring provided at the specified location to fix the reflecting member at said first position and a second flat face part being pressed by the plate spring to fix the reflecting member at said second position. When the fixation member is such a mounting hardware, it becomes possible to fix the reflecting member surely at the first position and the second position with a simple constitution.

Preferably, this fixation member is a mounting hardware integrated with the reflecting member, including a curved face part being capable of rotating while being pressed by a plate spring provided at the specified location. When the fixation member is such a mounting hardware, it becomes possible to rotate the reflecting member with a simple constitution.

Further, it is preferred that the apparatus of the present invention is mounted in an automatic analyzer analyzing ingredients in biological samples (specimens) such as blood or urine to be used. In the automatic analyzer of this case, for instance, the first containers are specimen containers for containing specimen and the second containers are reagent containers for containing reagent, and the first container setting part is a specimen rack for setting a plurality of specimen containers and the second container setting part is a reagent rack for setting a plurality of reagent containers.

EXAMPLE

Figure 5:
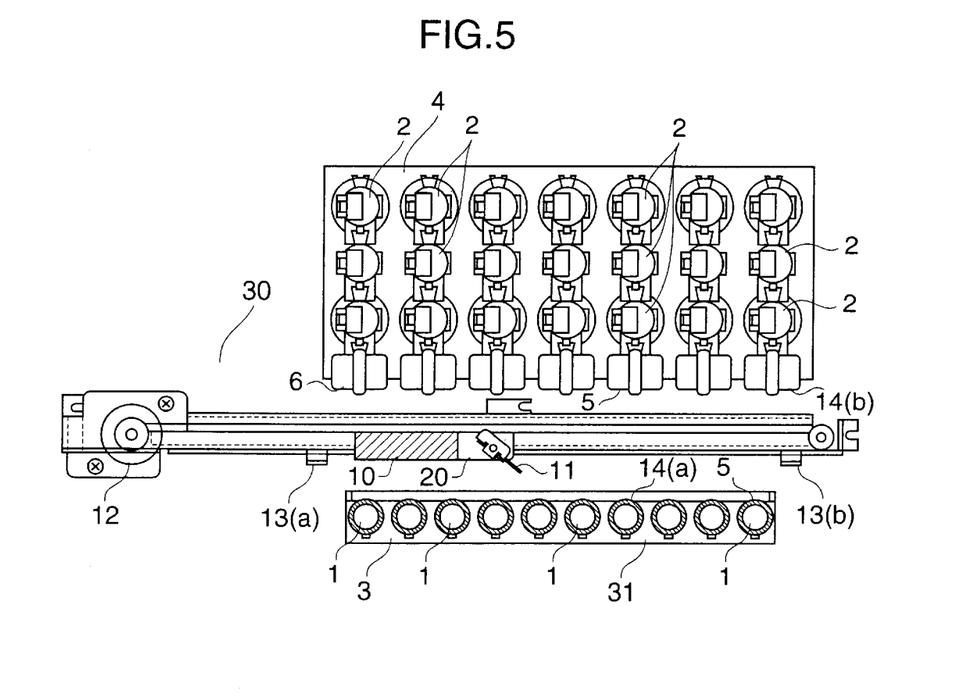
FIG. 5 is a top plan view of the automatic apparatus for reading bar codes of the embodiment of the present invention. (a specimen rack and a reagent holding part arranged on both sides of a travel path are illustrated together.)
Figure 6:
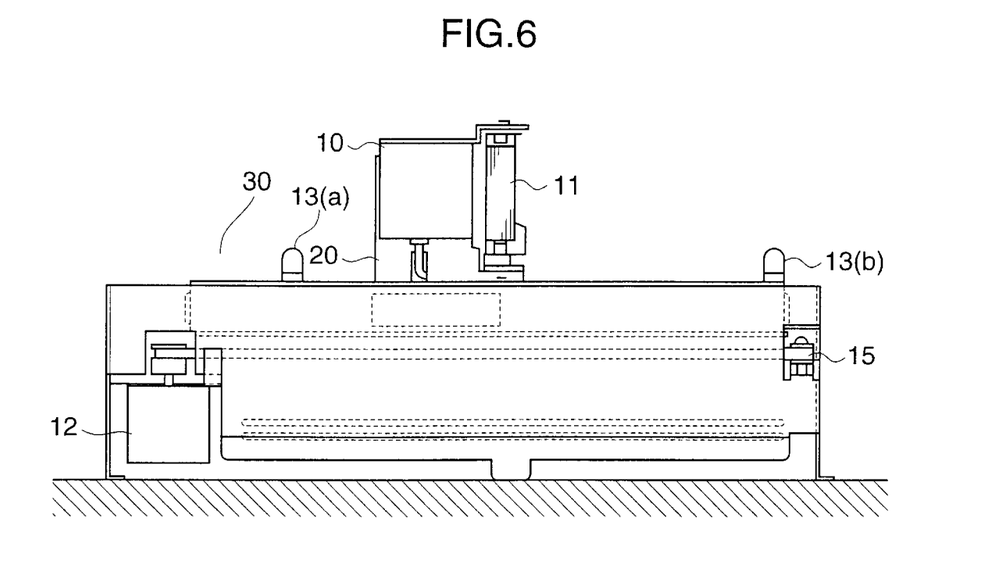
FIG. 6 is a front view of the automatic apparatus for reading bar codes of the embodiment of the present invention.
Figure 7:
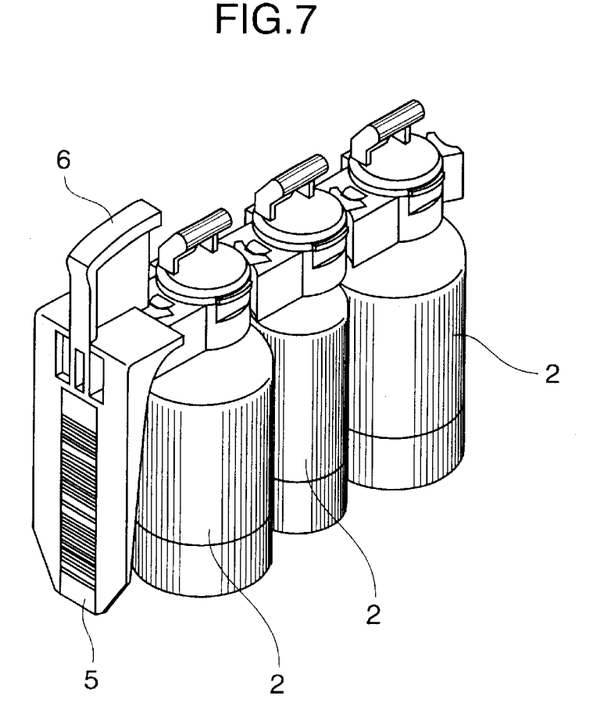
FIG. 7 is a perspective view of reagent containers and a reagent cassette used in the automatic apparatus for reading bar codes of the embodiment of the present invention.
Figure 8:
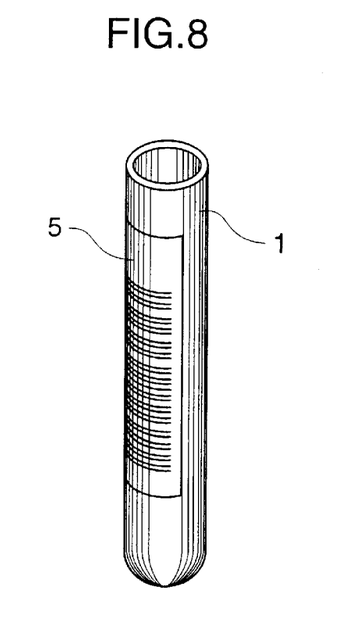
FIG. 8 is a perspective view of a specimen container used in the automatic apparatus for reading bar codes of the embodiment of the present invention.

FIGS. 1 to 4 are schematic views showing sequential motion of an automatic apparatus for reading bar codes in accordance with an embodiment of the present invention. FIG. 5 and FIG. 6 are a top plan view and a front view, respectively, of the automatic apparatus for reading bar codes in accordance with the embodiment of the present invention. FIG. 7 shows reagent containers and a reagent cassette in accordance with the embodiment of the present invention and is a perspective view of that stuck with bar codes. FIG. 8 shows a specimen container in accordance with the embodiment of the present invention and is a perspective view of that stuck with bar codes. FIG. 9 is a top plan view of the reflecting member and the bar code reader in accordance with the embodiment of the present invention and shows states of rotation of the reflecting member. FIG. 10 is a top plan view of a mirror mounting hardware in accordance with the embodiment of the present invention. FIG. 11 is a perspective view showing an essential part of the automatic analyzer in accordance with the embodiment of the present invention.

Thereinafter, referring to the drawings, there is illustrated an embodiment of an automatic analyzer provided with the automatic apparatus for reading bar codes of the present invention.

This automatic apparatus for reading bar codes utilizes a mirror 11 as a reflecting member and a stepping motor 12 as a driving means. A mirror 11 and a bar code reader 10 are integrated into one through a base 20. In FIGS. 5 and 6, said integrated base 20 may be moved linearly on a linear travel path through the medium of a belt 15 by rotation of the stepping motor 12.

A first and a second abutment parts 13(a), 13(b) illustrated in FIG. 5 are prisms attached onto said linear travel path.

In this example, the mirror 11 and a mirror mounting hardware 21 are integrated into one.

Figure 9A:
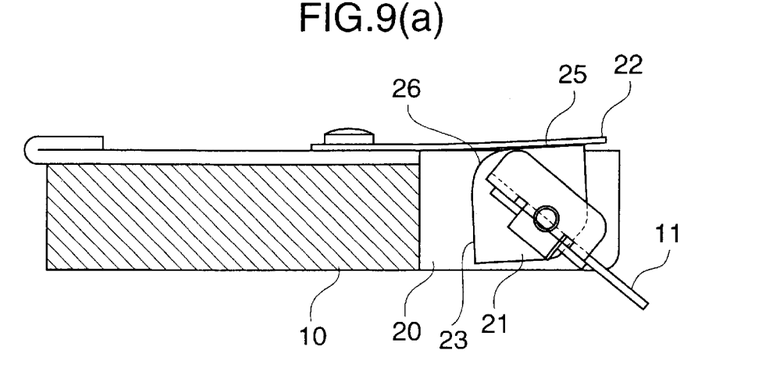
Figure 9B:
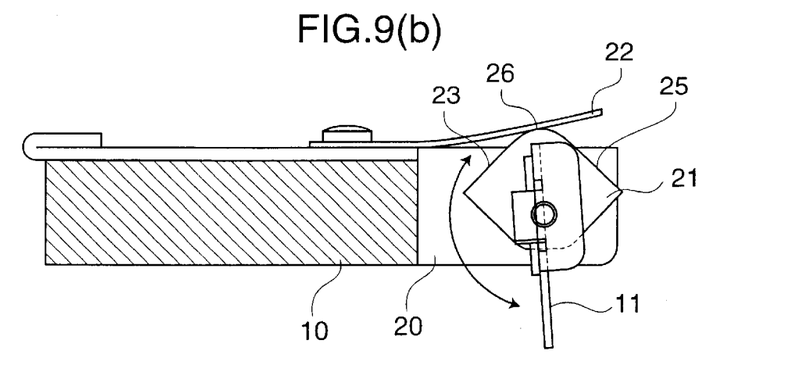
Figure 9C:
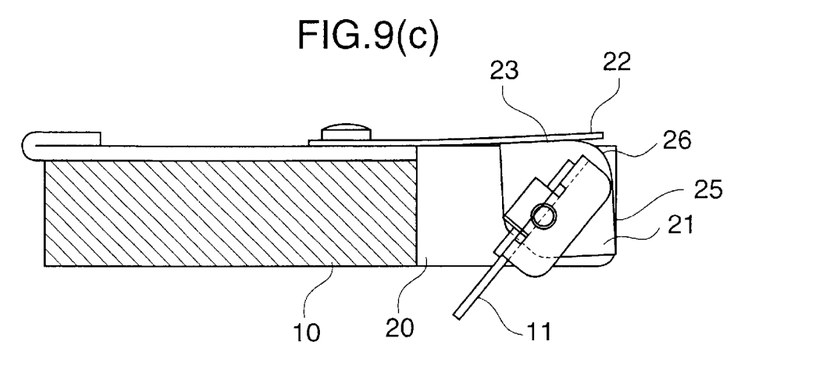
Figure 10:
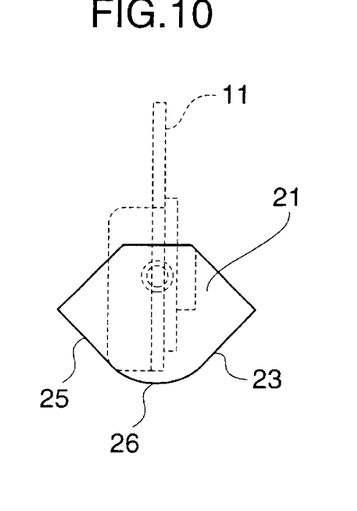
FIG. 10 is a top plan view of a mirror mounting hardware used in the automatic apparatus for reading bar codes according to the embodiment of the present invention.
Figure 11:
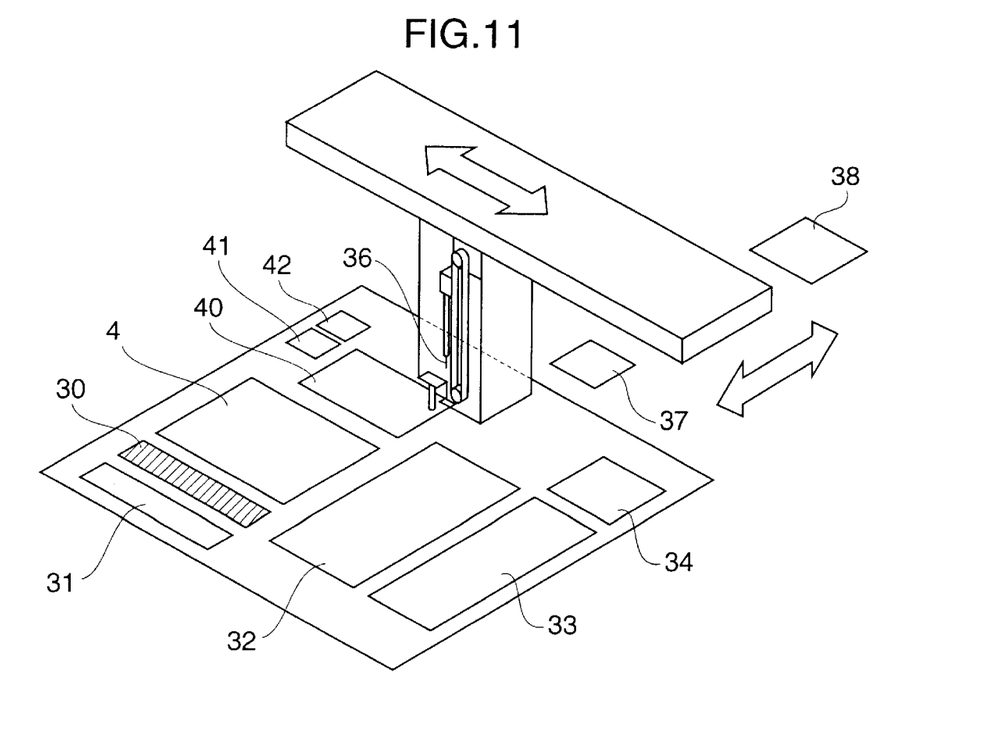
FIG. 11 is perspective view showing an essential part in mounting the automatic apparatus for reading bar codes according to the embodiment of the present invention to an automatic analyzer.

Contacting a first flat face part 25 of the mirror mounting hardware 21 illustrated in FIG. 9 and FIG. 10 with a plate spring 22 allows the mirror 11 mounted on the mirror mounting hardware 21 to retain a state as shown in FIG. 9(a). This state is a state in which the bar code reader 10 may read bar codes 5 stuck to a first bar code reading plane 14(a) through the medium of the mirror 11 (hereinafter, refer to as "state of reading").

Contacting a second flat face part 23 of the mirror mounting hardware 21 illustrated in FIG. 9 and FIG. 10 with the plate spring 22 allows the mirror 11 to retain a state as shown in FIG. 9(c). This state is a state of reading of a second bar code reading plane 14(b).

When the mirror 11 contacts the second abutment part 13(b), as shown in FIG. 9(b), a curved face part 26 of mirror mounting hardware 21 pushes the plate spring 22 and the mirror 11 rotates since the mirror 11 is applied with torque.

FIG. 8 is a perspective view of the specimen container 1. The specimen container 1 is stuck with the bar code 5 on a side face thereof and set at a specimen rack 3. Bar codes 5 are arranged on the first bar code reading plane 14(a) by setting specimen containers 1 at the specimen rack 3 illustrated in FIG. 5. Incidentally, in FIGS. 1 to 4, bar codes 5 are positioned perpendicularly in conformity with bar code reading planes 14(a), 14(b).

In FIG. 7, a plurality of reagent containers 2 are configured so as to be able to be connected to each other and connected by a reagent cassette 6 stuck with the bar code 5. Bar codes 5 are arranged on the second bar code reading plane 14(b) by setting the connected reagent containers at a reagent holding part 4 shown in FIG. 5. Information of reagents, for instance, kinds of reagents, lot numbers and the like may be inputted in the bar code 5.

Thereinafter, motion of an automatic analyzer of the present embodiment is described. A basic constitution of a reaction system and a measuring system are the same as the previously known apparatus.

Reagent containers 2 and the reagent cassette 6 shown in FIG. 7 are stuck with bar codes 5 and set at the reagent holding part 4.

Further, a specimen rack 3 at which specimen containers 1 stuck with bar codes 5 are located is set at a specimen setting part 31. At this time, the manipulations are done so as to arrange the bar codes 5 on the second bar code reading plane 14(b).

Further, though, in FIGS. 1 to 4, bar codes 5 on the first bar code reading plane 14(a) and bar codes 5 on the second bar code reading plane 14(b) are indicated at the positions opposite to each other relative to the mirror 11, bar codes arranged at any positions between two abutment parts 13(a) and 13(b) may be read. Accordingly, when a distance between two abutment parts 13(a) and 13(b) is long, bar codes 5 has a higher degree of flexibility in an arrangement thereof.

All bar codes arranged on the first bar code reading plane 14(a) and the second bar code reading plane 14(b) may be read by operating an automatic apparatus 30 for reading bar codes. Operations of the automatic apparatus 30 for reading bar codes of this time is described below in detail, referring to FIGS. 1 to 4.

Figure 1:
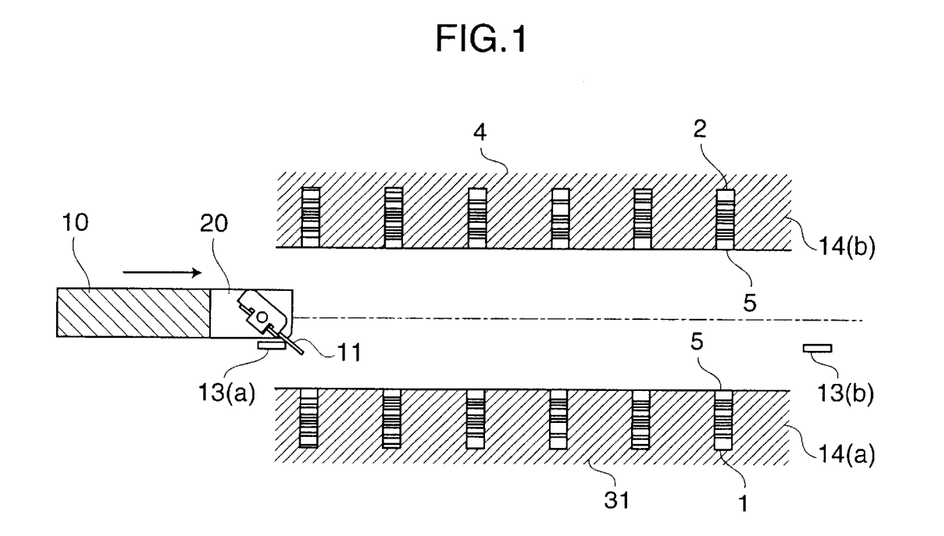
FIG. 1 is a schematic view showing motion of an automatic apparatus for reading bar codes of an embodiment of the present invention.

(1) At first, a state in which the mirror 11 contacts the first abutment part 13(a), as shown in FIG. 1, is taken as a initial state. The bar code reader 10 and the mirror 11 are integrated into one through the base 20 and controlled by a control part 38 (refer to FIG. 11) in such a way that this integrated part moves in the right direction in the drawing through the stepping motor 12. And, a state of the mirror 11 is a state of reading of the first bar code reading plane 14(a). From this state, the bar code reader 10 and the mirror 11 move in the right direction and thereby bar codes 5 stuck to the first bar code reading plane 14(a), that is, specimen containers 1 may be read in sequence.

Figure 2:
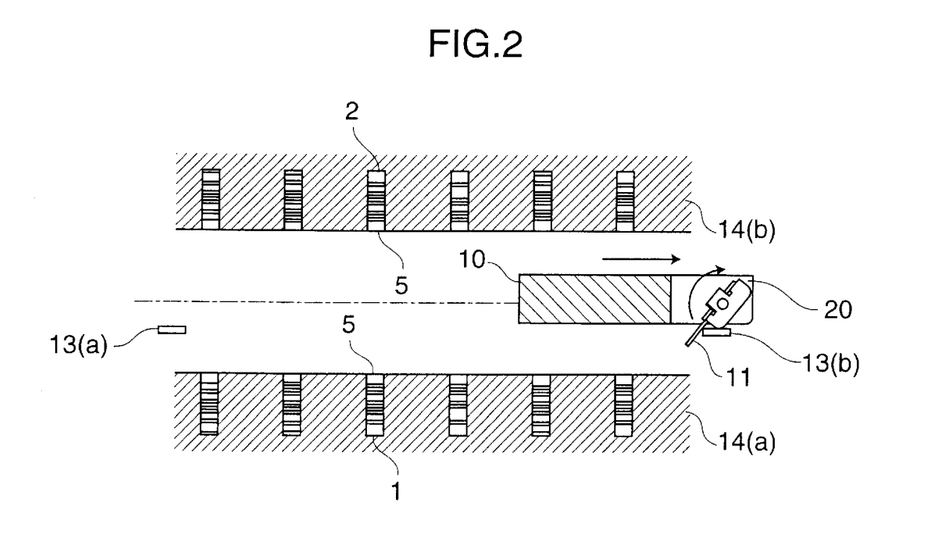
FIG. 2 is a schematic view showing motion of the automatic apparatus for reading bar codes of the embodiment of the present invention.

(2) An operation of the stepping motor 12 is stopped when the bar code reader 10 and the mirror 11 move in the right direction and reach the position as shown in FIG. 2. At this time, the mirror 11 is rotated up to the position as shown in FIG. 2 through contact with the second abutment part 13(b). Here, the automatic apparatus for reading bar codes 5 is controlled by the control part 38 so as to stop an operation of the stepping motor 12 when the mirror 11 reaches the position in which a state of the mirror 11 is a state of reading of the second bar code reading plane 14(b).

Figure 3:
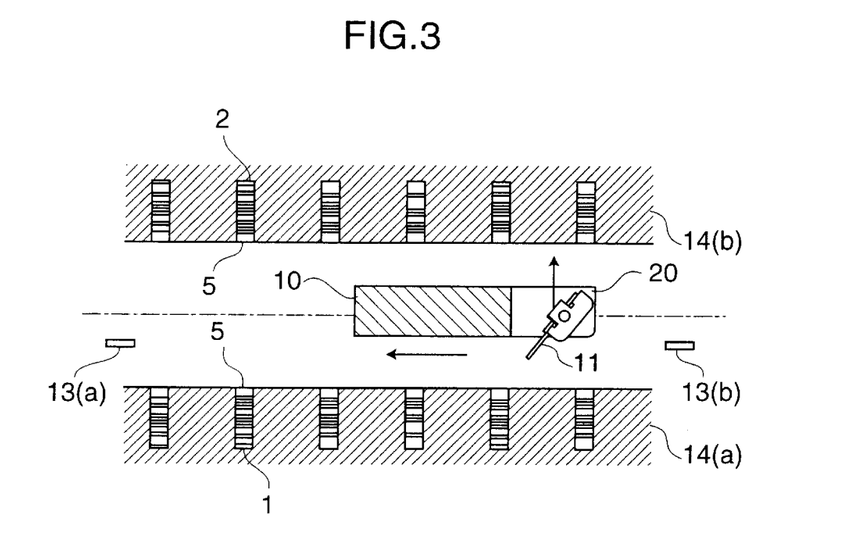
FIG. 3 is a schematic view showing motion of the automatic apparatus for reading bar codes of the embodiment of the present invention.

(3) Then, as shown in FIG. 3, the bar codes 5 stuck to the second bar code reading plane 14(b), that is, the reagent cassette 6 may be read in sequence by controlling the bar code reader 10 and the mirror 11 so as to move in the left direction with the control part 38.

Figure 4:
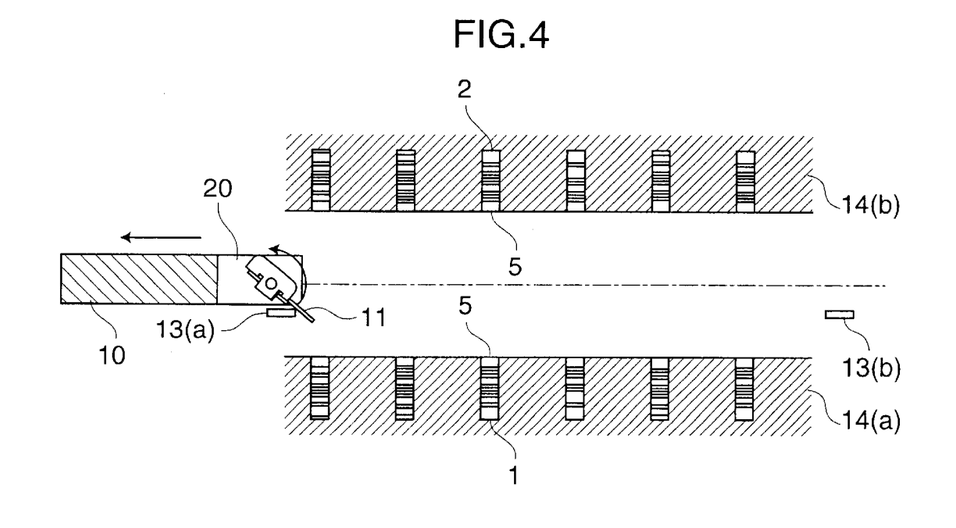
FIG. 4 is a schematic view showing motion of the automatic apparatus for reading bar codes of the embodiment of the present invention.

(4) When the bar code reader 10 and the mirror 11 move further in the left direction, they reach the state as shown in FIG. 4, and, in this state (i.e., the initial state as shown in FIG. 1), the automatic apparatus for reading bar codes 5 is controlled by the control part 38 so as to stop an operation of the stepping motor 12.

Thus, the bar codes 5 stuck to the first and the second bar code reading plane 14(a) and 14(b), that is, the reagent cassette 6 and the specimen containers 1, respectively, may be read with one bar code reader 10 and one stepping motor 12.

Referring now to FIG. 11, there is illustrated motion of the automatic analyzer after reading the bar code.

First, a pipette 36 draws in a specimen from the specimen container 1 and dispenses a reaction plate set at a reaction part 40 with the specimen.

And, the pipette 36 draws in a reagent from the reagent container 2 and dispenses the reaction plate dispensed with the specimen with the reagent.

And so, the content of the reaction plate is permeated and agitated, and incubated for a specified time of period.

Further, the pipette 36 draws in a sample incubated from the specimen and the reagent from the reaction plate and injects them in a sample measuring part 41, and the sample is measured.

Then, the pipette 36 is moved to a cleaning bath 42 and cleaned.

Thereafter, the reaction plate become unnecessary is moved to a reaction plate discarding part 34 by a reaction plate driving means 37 and discarded.

When a reagent has been replaced, a direction of replacing a reagent is inputted and only the bar code 5 of the reagent cassette 6 is read by the automatic apparatus 30 for reading bar codes. In addition, when a specimen is set newly, only the bar code 5 of the specimen container 1 is read by the automatic apparatus 30 for reading bar codes.

Since the automatic apparatus for reading bar codes of the present invention is configured as described above in detail, it is possible to read bar codes stuck to first containers and second containers with one bar code reader and one driving means, and since a degree of flexibility in setting positions of the first containers and the second containers is enhanced, it is possible to achieve the simplification, the miniaturization and the lower prices of the apparatus.

DESCRIPTION OF REFERENCE CHARACTER 1 specimen container
2 reagent container
3 specimen rack
4 reagent holding part
5 barcode
6 reagent cassette
10 bar code reader
11 reflecting member (mirror)
12 stepping motor
13 abutment part
14 bar code reading plane
15 belt
20 base
21 mirror mounting hardware
22 plate spring
23, 25 flat face part of mirror mounting hardware
26 curved face part of mirror mounting hardware
30 schematic view of an automatic bar code reader
31 specimen setting part
33 reaction plate setting part
34 reaction plate discarding part
36 pipette
37 reaction plate driving means
38 control part
40 reaction part
41 sample measuring part
42 cleaning bath

What is claimed is:

1. An automatic apparatus for reading bar codes comprising a bar code reader for reading bar codes stuck to containers, a reflecting member for reflecting light irradiated from the bar code reader to the bar codes, a driving means for moving the reflecting member to and from in the direction of the light irradiated from the bar code reader and in the reverse direction thereof on a travel path parallel to the direction of the irradiated light and at least one abutment part provided on said travel path for regulating the range of travel of the reflecting member, wherein a first container setting part for setting first containers stuck with first bar codes and a second container setting part for setting second containers stuck with second bar codes are arranged on both sides, respectively, of said travel path; the reflecting member is provided in such a way that the reflecting member may rotate between a first position to allow said bar code reader to read the first bar codes of the first containers set at the first container setting part through the medium of the reflecting member and a second position to allow said bar code reader to read the second bar codes of the second containers set at the second container setting part through the medium of the reflecting member; and by moving the reflecting member to and from in said way with said driving means, the reflecting member contacts said abutment part to rotate from said first position to said second position or from said second position to said first position and thereby said bar code reader reads the first bar codes and the second bar codes.

2. An automatic apparatus for reading bar codes as set forth in claim 1, wherein the reflecting member is a reflecting mirror.

3. An automatic apparatus for reading bar codes as set forth in claim 1, wherein the driving means is a stepping motor for driving a power transmission belt.

4. An automatic apparatus for reading bar codes as set forth in claim 1, wherein the first containers are specimen containers for containing specimen and the second containers are reagent containers for containing reagent, and the first container setting part is a specimen rack for setting a plurality of specimen containers and the second container setting part is a reagent rack for setting a plurality of reagent containers.

5. An automatic apparatus for reading bar codes as set forth in claim 1, wherein the bar code reader and the reflecting member are integrated into one.

6. An automatic apparatus for reading bar codes as set forth in claim 1, wherein the abutment part consists of a first abutment part acting in such a way that the reflecting member takes said first position and the second abutment part acting in such a way that the reflecting member takes said second position.

7. An automatic apparatus for reading bar codes as set forth in claim 1, further comprising a fixation member for fixing the reflecting member at said first position and said second position.

8. An automatic apparatus for reading bar codes as set forth in claim 7, wherein the fixation member is a mounting hardware integrated with the reflecting member, including a first flat face part being pressed by a plate spring provided at the specified location to fix the reflecting member at said first position and a second flat face part being pressed by the plate spring to fix the reflecting member at said second position.

9. An automatic apparatus for reading bar codes as set forth in claim 7, wherein the fixation member is a mounting hardware integrated with the reflecting member, including a curved face part being capable of rotating while being pressed by a plate spring provided at the specified location.

10. An automatic analyzer provided with the automatic apparatus for reading bar codes as set forth in claim 4.

11. An automatic apparatus for reading bar codes comprising:
    a bar code reader for reading bar codes stuck to containers;
    a mirror for reflecting light irradiated from the bar code reader in a first reflecting direction and in a second reflecting direction;
    a base for carrying the bar code reader and the mirror;
    a driving means for moving the base linearly in a direction of the light irradiated from the bar code reader and in a direction reverse to said direction; and
    an abutment part provided at such a position that the abutment part comes in contact with the mirror by linear movement of the base,
    wherein the first reflecting direction and the second reflecting direction are perpendicular to the directions in which the base is linearly moved,
    the mirror rotates by contact with the abutment part to change a reflecting direction of the light irradiated from the bar code reader from said first reflecting direction to said second reflecting direction or from said second reflecting direction to said first reflecting direction.

12. An automatic apparatus for reading bar codes as set forth in claim 11, wherein the abutment part comprises a first abutment part provided for reflecting the light irradiated from the bar code reader to said first reflecting direction and a second abutment part provided for reflecting the light irradiated from the bar code reader to said second reflecting direction.

13. An automatic apparatus for reading bar codes as set forth in claim 12, wherein the base is moved linearly between the first abutment part and the second abutment part.

14. An automatic apparatus for reading bar codes as set forth in claim 11, wherein the containers are reagent containers and specimen containers.

15. An automatic apparatus for reading bar codes as set forth in claim 14, wherein the bar code reader reads the bar codes stuck to the specimen containers when the base is moved linearly in the direction of the light irradiated from the bar code reader and reads the bar codes stuck to the reagent containers when the base is moved linearly in the direction reverse to the direction of the light irradiated from the bar code reader.

16. An automatic apparatus for reading bar codes as set forth in claim 14, wherein the bar code reader reads the bar codes stuck to the reagent containers when the base is moved linearly in the direction of the light irradiated from the bar code reader and reads the bar codes stuck to the specimen containers when the base is moved linearly in the direction reverse to the direction of the light irradiated from the bar code reader.

17. An automatic apparatus for reading bar codes as set forth in claim 11, wherein the driving means is a stepping motor for driving a power transmission belt.

18. An automatic apparatus for reading bar codes as set forth in claim 11, further comprising a fixation member for fixing the mirror in two statuses.

19. An automatic analyzer provided with an automatic apparatus for reading bar codes as set forth in claim 11.

* * * * *